(12) United States Patent
Vilsmeier

(10) Patent No.: US 10,022,559 B2
(45) Date of Patent: Jul. 17, 2018

(54) METHOD AND DEVICE FOR IMPROVED RADIATION THERAPY TREATMENT OF A SET OF TARGETS

(71) Applicant: Brainlab AG, Munich (DE)

(72) Inventor: Stefan Vilsmeier, München (DE)

(73) Assignee: Brainlab AG, Munich (DE)

( * ) Notice: Subject to any disclaimer, the term of this patent is extended or adjusted under 35 U.S.C. 154(b) by 152 days.

(21) Appl. No.: 15/024,294

(22) PCT Filed: Sep. 8, 2014

(86) PCT No.: PCT/EP2014/069021
§ 371 (c)(1),
(2) Date: Mar. 23, 2016

(87) PCT Pub. No.: WO2015/039903
PCT Pub. Date: Mar. 26, 2015

(65) Prior Publication Data
US 2016/0331997 A1    Nov. 17, 2016

Related U.S. Application Data

(63) Continuation-in-part of application No. PCT/EP2013/002846, filed on Sep. 20, 2013.

(51) Int. Cl.
*A61N 5/10* (2006.01)
*G06F 19/00* (2018.01)

(52) U.S. Cl.
CPC ........... *A61N 5/103* (2013.01); *A61N 5/1069* (2013.01); *A61N 5/1077* (2013.01); *G06F 19/3481* (2013.01)

(58) Field of Classification Search
None
See application file for complete search history.

(56) References Cited

U.S. PATENT DOCUMENTS

2008/0298550 A1* 12/2008 Otto ........................ A61N 5/103
378/65

FOREIGN PATENT DOCUMENTS

WO      2013075743      5/2013

OTHER PUBLICATIONS

Bortfeld, et al., Optimized planning using physical objectives and constraints, Seminars in Radiation Oncology, Saunders, Philadelpha, PA, US. Jan. 1, 1999.
(Continued)

*Primary Examiner* — Hoon Song
(74) *Attorney, Agent, or Firm* — Middleton Reutlinger

(57) ABSTRACT

A medical data processing method for determining a target set comprising at least one irradiation target in a patient's body for radiation therapy treatment by means of a treatment device constituted to treat the at least one target by means of one or more sub-beams during a treatment time, the one or more sub-beams constituting at least one treatment beam which is to pass through the at least one target in accordance with a treatment plan during the treatment time, the method comprising the following steps and being constituted to be executed by a computer: a) acquiring (S 1.1) critical area; b) acquiring (S 1.2) target data; c) acquiring (S 1.3) treatment beam constraint data; d) acquiring treatment beam criteria data (S 1.4); and e) determining (S4), based on the critical area data, the target data, the treatment beam constraint data and the treatment beam criteria data, target set data describing spatial information on at least one irradiation region.

15 Claims, 4 Drawing Sheets

(56) References Cited

OTHER PUBLICATIONS

Kang, Jun, et al., A Method for optimizing Linac treatment geometry for volumetric modulated arc therapy of multiple brain metastases, Medical Physics, AIP, vol. 37, No. 8, Melville, NY, US. Jul. 20, 2010.

European Patent Office, International Search Report for PCT/EP2014/069021, pp. 1-4, Rijswijk, NL. Nov. 17, 2014.

* cited by examiner

//  = US 10,022,559 B2 =

METHOD AND DEVICE FOR IMPROVED RADIATION THERAPY TREATMENT OF A SET OF TARGETS

The present invention is directed to a medical data processing method of determining a target set comprising at least one irradiation target which is to be treated by treatment radiation. Furthermore, the invention is directed to a medical data processing method of planning radiation therapy treatment of the at least one target contained in the target set (for example for determining a corresponding treatment plan), wherein the radiation therapy treatment is conducted for example by means of a treatment beam source and a treatment beam shaping device which directs a treatment beam to a set of targets in or on a patient's body. Preferably, the treatment plan is determined based on the result determined by executing the medical data processing method of determining a target set.

When planning a radiotherapy treatment, it is generally desirable to exclude risk regions such as organs-at-risk (OARs) from a target region which is to be irradiated with treatment radiation. This may be difficult for example in cases in which there are multiple spatially disjunct targets to be irradiated or in which a coherent and/or continuous target at least partially surrounds a risk region (e.g. in the case of the target region comprising the prostate or certain brain structures). WO 2013/0754743 discloses a data processing method for determining a treatment plan in which each spatially disjunct target is irradiated with for example an individual treatment beam and wherein the time interval during which each of the targets is irradiated and/or the beam geometry is (are) varied so that each target is sufficiently irradiated while avoiding damage to risk regions during relative movement of the patient's body and the treatment beam source. Depending on the geometry, this may however still lead to at least some irradiation of risk regions with treatment radiation.

The present invention therefore provides a medical data processing method for determining a target set comprising at least one irradiation target (which can be a metastasis) which allows to irradiate multiple targets while effectively avoiding irradiation of risk regions.

Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can for example be added to said other embodiment.

EXEMPLARY SHORT DESCRIPTION OF THE PREFERRED FEATURES PRESENT INVENTION

In this section, a short description of exemplary features of the present invention is given which shall not be understood to limit the invention only to the features and combinations of features described in this section.

The present invention provides a medical data processing method of determining a target set comprising at least one irradiation target ("set target") based on known constraints on anatomical body parts which shall be irradiated and anatomical body parts which shall not be irradiated. The target set is described by target set data which also describes an irradiation region in which the at least one set target is positioned based on predetermined information about a possible treatment beam arrangement. The at least one set target is preferably selected based on information about its spatial relationship to its nearest neighboring irradiation target, for example in case multiple metastases need to be treated. Alternatively or additionally, the set targets can be selected based on the type of envisaged radiotherapy treatment. The target set data can be used as a mask, for example a constraint mask, which can be overlaid on a planning target volume (which describes the anatomical body part, for example an organ such as the prostate or at least part of the brain) to differ between regions which shall be irradiated (irradiation regions) and regions which shall not be irradiated (non-irradiation regions). The constraint imposed by the mask therefore is to what degree a region shall be irradiated. The degree may be binary (e.g. either full irradiation or no irradiation at all) or may be divided into more bins which allow for more than two degrees of irradiation. This mask can be used for example as a boundary condition for subsequent generation of a radiotherapy treatment plan, i.e. it cannot be changed during generation of the treatment plan.

GENERAL DESCRIPTION OF THE PRESENT INVENTION

In this section, a description of the general, in some cases particular preferred, features of the present invention is given.

For example the present invention provides a data processing method for determining target set data describing a target set comprising at least one irradiation target. Furthermore, the invention also relates to a method (for example a data processing method, more particularly medical data processing method) for determining, based on the target set data, a treatment plan for radiation therapy treatment of targets.

An envisaged radiotherapy treatment can be directed to irradiating at least one irradiation target to be treated, for example to treating a plurality of such irradiation targets. In the case of plural targets, the treatment device is preferably constituted to treat the targets (which are for example two or more targets, as a further example three or more targets or four or more targets), at least one of simultaneously and sequentially. Furthermore, preferably a set of irradiation targets to be treated (called target set) is determined. The number of irradiation targets in the target set (called set targets) can be equal to the total number of irradiation targets to be irradiated during the treatment (which is the case for example if there is only one irradiation target to be treated) or less than the total number of irradiation targets (the latter case is in the framework of this disclosure also called "real subset"). For example, the target set is not empty, i.e. it comprises at least one irradiation target. The target set and is preferably described by target set data which is preferably acquired as part of the disclosed method. For such a description, the target set data may contain information about for example the position(s) of the irradiation target(s) contained in the subset. The position(s) can be defined in a coordinate system which rests relative to the patient's body and/or relative to the treatment beam source. Alternatively, the position(s) can be defined in a coordinate system which is not defined to rest relative to the patient's body or the treatment beam source but which is used as a global coordinate system for processing positional data during generation of a radiotherapy treatment plan.

CONSTRAINT MASK GENERATION

If the envisaged radiation therapy treatment comprises irradiating only one irradiation target, that irradiation target is determined to be a set target. Preferably, a target set comprising a plurality of irradiation targets is determined based on comparing the spatial relationship between neighboring irradiation targets which can be determined based on (for example known and/or acquired) information about the positions of the irradiation targets which is contained in target position data previously acquired during execution of the data processing method. For example, from a plurality of irradiation targets, only those are selected as set targets which have a distance from its nearest neighbour which does not exceed a predetermined distance. Alternatively or additionally, only those irradiation targets may be selected as set targets which lie in a predetermined (i.e. known) volume. That volume may for example be applied as a boundary condition for the positions of the set targets if it has a predetermined spatial relationship (i.e. at least one of position and orientation) relative to at least one other (for example predetermined) irradiation target which is not selected as a set target. The volume may alternatively or additionally be defined to be a volume in which no risk region is present. In that case, the volume (also called target volume) may be used as a kind of mask which is applied to the patient's body, and all irradiation targets lying within the volume are determined to be irradiated, for example simultaneously irradiated (alternatively, the set targets may also be determined to be sequentially irradiated and the target set data may then merely prescribe that the set targets shall be irradiated and the set targets may then be treated as individual targets which are used as spatially separate targets in the inventive medical data processing method of determining a treatment plan). The target set data can thus be used as a mask, for example a constraint mask, which can be overlaid on a planning target volume (which describes the anatomical body part, for example an organ such as the prostate or at least part of the brain) to differ between regions which shall be irradiated (irradiation regions) and regions which shall not be irradiated (non-irradiation regions). The constraint imposed by the mask therefore is to what degree a region shall be irradiated. The degree may be binary (e.g. either full irradiation or no irradiation at all) or may be divided into more bins which allow for more than two degrees of irradiation. This mask can be used for example a as boundary condition for follow-up data processing, for example for subsequent generation of a radiotherapy treatment plan, i.e. it cannot be changed during generation of the treatment plan.

Alternatively or additionally, the set targets may be selected based on information about the envisaged radiotherapy treatment, for example based on information about an anatomical body part on which the radiotherapy treatment is to be carried out.

Preferably, critical area data is acquired which describes the position of any risk region present in the patient's body and/or in the planning target volume (PTV), i.e. the volume of the patient's body which is assessed during generation of a treatment plan (embodied by an anatomical structure, for example the prostate or at least a part of the brain). The critical area data as well as the target data, treatment beam constraint data and treatment beam criteria data described below serve as a basis for determining the target set data and on that basis target volume data describing the position of the target volume within which irradiation is prescribed (i.e. mandatory) when generating a corresponding treatment plan. This supports to determine a target set comprising irradiation targets which may be simultaneously irradiated while avoiding undesired irradiation of a risk region. The other irradiation targets can then be irradiated after a change in relative position between the patient's body and the treatment device (for example the treatment beam source, for example along an arc-shaped curve relative to the patient's body) before the set targets are irradiated or after they have been irradiated. For example, certain treatment beam directions (defined for example as an angular interval) relative to the patient's body and/or the irradiation targets can be determined which allow for the desired coverage of the volume while omitting any existing risk region.

When a radiation therapy treatment plan is determined based on the target set data, the at least one set target serves as the at least one target to be irradiated during the envisaged radiation therapy. In case the target set comprises a plurality (for example at least two) set targets, the set targets preferably are spatially separate, i.e. three-dimensionally disjunct (non-overlapping in space). For example, an algorithm for generating the treatment plan is bound by the target set data, i.e. it cannot change the constitution of the target set. For example, it cannot change the number or type of set targets or choose not to prescribe irradiation of the set targets. Further particularly, the algorithm is forced to determine that the set targets shall be irradiated. The target set data thus serves for example as a mask which is overlaid on the planning target volume in the sense that all parts of the planning target volume comprising a set target are assigned to an irradiation region (i.e. a region which is prescribed during later generation of a treatment plan as mandatory for irradiation in consideration of the possibilities offered by the treatment beam arrangement) and that all parts of the planning target volume which do not comprise a set target are allowed to be assigned to a non-irradiation region (i.e. a region which may during later generation of a treatment plan may be prescribed to be not irradiated). The spatial extent of an irradiation region and a non-irradiation region, respectively, is determined in dependence on the geometric possibilities allowed by the treatment beam arrangement and for example the beam geometry. Thus, the target set data contains information on the spatial information, for example the position(s) and geometry (for example shape and size or volume, respectively), of the irradiation region(s) and—according to a further, less preferred embodiment—non-irradiation region(s).

The radiation therapy treatment is performed by means of at least one treatment beam which is issued by the treatment device during a treatment time (which corresponds for example to the time of a radiotherapy treatment session). In more detail, the at least one target contained in the target set is preferably treated by at least one sub-beams which is comprised by the at least one treatment beam. For example, one sub-beam is preferably are assigned to treat each only a respective one of the irradiation targets (for example in a bijective assignment between irradiation targets and sub-beams). Alternatively, one sub-beam can be assigned to treat all of the set targets, and at least one sub-beam can be assigned to at least one other irradiation target (for example in a bijective assignment). The treatment is performed in accordance with the above-mentioned treatment plan (which can be characterised by for example a corresponding treatment beam arrangement). Preferably, a specific one of the sub-beams is dedicated to treat a specific one of the irradiation targets or all of the set targets in accordance with the treatment plan.

According to a specific and less preferred embodiment, the treatment device is constituted to issue at least two of the sub-beams simultaneously in order to allow for a simultaneous treatment of at least two bijectively assigned irradiation targets at least for a time interval during the treatment time so that the treatment time can be shortened. For example, the treatment device is constituted to allow for simultaneous treatment of sub-beam all irradiation targets contained in the target set at least during a time interval during treatment time. The treatment device is for example constituted to issue spatially separate sub-beams for simultaneous treatment of the irradiation targets. For example, determining the treatment plan can comprise determining a set of the at least two targets (corresponding to the aforementioned target set comprising exactly two set targets). The set can comprise all or less than all of the treatment targets and the number of targets within the target set can change during the treatment time as described in more detail below. The determined treatment plan for example describes the treatment of the target set (see below).

The treatment plan (i.e. the radiation therapy treatment plan) is preferably determined based on the target set data (i.e. for example after execution of the method for determining the target set data, preferably the method of determining a treatment plan comprises execution of the method for determining the target set data), and therefore also based on the target data, treatment beam constraint data and treatment beam criteria data which will be described below. The target data describe for example the entirety of irradiation targets, preferably it describes their positions. If the target data comprises more than one target, those targets are for example spatially separate targets, i.e. the targets are for example three-dimensionally disjunct. For example, the treatment plan is determined to fulfil the constraints described by the treatment beam constraint data and the criteria described by the treatment beam criteria data. As far as herein the geometry (size and/or shape) of a sub-beam is described, for example the geometry of a cross-sectional area, this refers for example to the shape, the sub-beam has within the patient's body (for example after passing through a beam shaping device).

The above-mentioned target data describe spatial information on the at least two targets which are for example spatially separate within the patient's body. The spatial information describes for example the geometries (size and/or shape) of the targets and/or the positions of the targets.

The target data provides for example the spatial information about volume in space which has to absorb radiation so as to treat targets. The positions of the irradiation targets (also simply called "targets") are preferably described in a reference system in which potential treatment beam arrangements (i.e. treatment beam arrangements which can be realized by the treatment device) are at rest, for example the position is described relative to the treatment device. The positions of the targets can also be described in other reference systems. For instance, the positions of the targets can be described in a reference system in which the targets are at rest. In that case, the treatment plan (treatment beam arrangement) is preferably described in a reference system in which the targets are at rest. Of course, transformations between different reference systems can be performed and are for example described by the target data.

As already mentioned above, the treatment beam arrangement can comprise one or more treatment beams which in turn may comprise at least one, preferably two or more spatially separated sub-beams for at least a time interval during treatment. It is to be noted, that simultaneous treatment of multiple targets by multiple sub-beams allows a significant decrease in treatment time compared with successive treatment of single targets. Therefore, according to the present invention, it is preferred to have a treatment beam which comprises at least two sub-beams which allow simultaneous treatment of at least two targets, one target being embodied for example by the entirety of set targets and one target preferably lying a non-irradiation region. The at least two sub-beams can be generated from a beam issued from a single treatment beam source, for example by blocking part of the beam by means of a beam shaping device (for instance a multi-leaf collimator) for example for conformal shaping of the treatment beam and/or by using two different sub-treatment beam sources each of which issuing one of the two sub-beams (in other words the treatment beam source comprises two sub-treatment beam sources [which for example can be moved independently or dependently]). Preferably, the treatment beam source is movable in order to generate (for example in combination with a beam shaping device) the treatment radiation (which has spatial and/or time features) in accordance with the treatment plan, i.e. treatment beam arrangement (determined in accordance with the present invention), targets (or at least one target and the volume comprising, for example defining, the target set) seen from the direction of the treatment beam source may "overlap" for a certain period of time during movement of the beams source so that spatially separate sub-beams directed to those targets may then merge for that period of time. A sub-beam which results from merged sub-beams which were formerly respectively dedicated to the treatment of just one target treats for example more than one target, i.e. all the targets which were formerly independently treated by the merged sub-beams. Therefore, the treatment beam can comprise at least two (integral) sub-beams which are spatially separate for at least a time interval during treatment and which can merge for a certain time interval during treatment. The present invention is for example directed to determine a treatment beam arrangement which is optimized for the treatment of spatially separate targets by means of sub-beams.

Based on the output of the inventive data processing method, a treatment plan (for example a treatment beam arrangement) for simultaneous treatment of a set of at least two target sets is determined based on the treatment beam constraint data, the treatment beam criteria data and the target set data. Preferably, the treatment plan is determined further based on target data. Preferably, at least two targets are simultaneously treated by at least two sub-beams at least during a time interval during treatment. The radiation therapy treatment is performed during the time referred to as "treatment time" and corresponds for example to a treatment session (also called "fraction") which is performed during the treatment time. Since the treatment beam arrangement for simultaneous treatment of the above-mentioned set of at least two targets depends for example on the set of at least two targets and vice versa, the inventive method comprises for example determining the set of at least two target sets for which a treatment beam arrangement can be determined (which fulfils the constraints described by the treatment beam constraint data and the criteria described by the treatment beam position data). The at least two target sets each comprise for example only targets which can (potentially) simultaneously be treated for the whole treatment time in accordance with one or more of the potential treatment beam arrangements.

Particularly, the treatment beam source can move relative to the targets which, seen from the direction of the beam source, may change the geometry, for example outline, of the targets. For example, the position of the patient's body may kept constant in a global coordinate system (in which neither the patient's body nor the treatment device for example the treatment beam source—are defined to rest) and the treatment device (for example the treatment beam source) may be moved in the global coordinate system, or the patient's body may be move in the global coordinate system while keeping the position of the treatment device (for example the treatment beam source) constant in the global coordinate system. According to an even further embodiment, both the patient's body and the treatment device (for example the treatment beam source) may be moved in the global coordinate system Preferably, the treatment beam device is constituted to change the cross-sectional geometry of sub-beams directed to such target sets when the treatment beam source and the patient's body are moved relative to one another for example so as to make sure that the target sets absorb the treatment beam over the whole cross-sectional area from each direction the treatment beam source is directed to the targets. Preferably, the beam is shaped in such a way that, if the at least two target sets are projected into a plane (projection plane) perpendicular to the beam direction of a spatially separate one of the one or more sub-beams and if the cross sectional area of the spatially separate sub-beam is projected into the plane, then no more than one of the at least two projected spatially separate target sets lies spatially separate within the projected cross sectional area, for example at least for no longer than a predetermined time. This criterion (referred to as "not more than one target" criterion) is considered to be an example of the radiation reduction criterion described in more detail below.

For example, the treatment beam constraint data describes constraints for possible (potential) treatment beam arrangements, and for example describes spatial information on the possible treatment beam arrangements for example in a reference system in which the treatment device is at rest. The constraints are for example technical constraints which describe possible relative positions between the beam source and the patient (for example the targets) which are made possible by the treatment device. The treatment beam constraint data describe for example information on possible configurations and/or positions of a beam shaping device, particularly a collimator, specifically a multi-leaf collimator, shaping the cross-sectional shape of the beam, and/or on possible positions of the beam source relative to the at least two targets (e.g. due to a limited range of movement of the beam source for instance along a path and/or a limited range of movement of a couch on which the patient is lying). In other words, such constraints are "technical" constraints which are concerned with the feasibility of generating a treatment beam arrangement. The feasible treatment beam arrangements are referred to herein as "potential treatment beam arrangements". In other words, potential treatment beam arrangements are arrangements which can be realized by the treatment device but which can or cannot violate the medical criteria. It is to be understood that each beam shaping device which forms the cross-sectional shape of the beam generated by the beam source is subjected to certain technical borders for at least a time interval during treatment. For example, a multi-leaf collimator which can be used as a beam shaping device, is not able to generate separate sub-beams at least part of which lies in a direction parallel to the direction the leaves of the multi-leaf collimator are moved. Moreover, constraints of features of an arrangement of at least one treatment beam can include information on possible positions of a beam source relative to the at least two targets. For example, one or more target may be located outside of an area which can be covered by means of a treatment beam generated by means of a treatment beam source in a certain position (location and/or orientation) relative to the target/targets, wherein, when the treatment beam source is moved to another position, said target or targets are located within the area covered by the beam.

The treatment beam criteria data for example relates to medical criteria for treating spatially separate target sets. Those criteria for example describe that parts outside the target sets (referred to as "outside body parts") are preferably not affected by treatment radiation due to limited options available in accordance with the treatment beam constraint data. In accordance with the invention, the treatment beam criteria data described below are applied in order to determine the treatment plan. The treatment beam criteria data for example describe a criterion referred to as "radiation reduction criterion" according to which the exposure of outside body parts to radiation (in the following also referred to as "exposure") is to be reduced, if possible (and for example if the reduction is more than a predetermined extent) by performing a non-simultaneous treatment instead of a simultaneous treatment of the at least two target sets. That is, a reduction (for example a reduction by the predetermined extent or more) has for example higher priority than a simultaneous treatment of all of the at least two target sets during treatment. "Allowing for the determination of a non-simultaneous treatment plan" means for example that the reduction of the exposure (of the outside body parts for example of at least to the predetermined extent) is given higher priority than simultaneous treatment of all of the at least two target sets when determining the (optimised) treatment plan. A reduction of exposure means for example that the volume (filled with outside body parts and not including the at least two targets and also referred to as "healthy volume") and subjected to treatment radiation is to be reduced, if such a reduction can be achieved by non-simultaneous treatment instead of simultaneous treatment and for example if such a reduction is equal to or more than a predetermined extent. This healthy volume refers for example to a volume which is or comprises volume in between of two or more or all of the at least two target sets. The healthy volume can for example be a volume within a gap between two target sets which volume is subjected to treatment radiation if the two target sets are treated simultaneously by (only one spatially separate) sub-beam. If one wants to treat all of the at least two target sets simultaneously for the treatment time (i.e. the total time of treatment), then it can be unavoidable to subject healthy volume between the target sets to the treatment radiation due to the constraints described by the treatment beam constraint data. Nevertheless, a reduction of the healthy volume subjected to the radiation would be desirable. According to the radiation reduction criterion it is allowed (that is for example allowed, for example preferred, or for example a must) that a treatment plan (referred to as "non-simultaneous treatment plan") is determined which describes a non-simultaneous treatment if this non-simultaneous treatment results in a reduction of the exposure, for example in a reduction of the healthy volume (volume filled with outside body parts)

subjected to the treatment radiation of the at least one treatment beam, for example at least in a reduction in a predetermined extent. The non-simultaneous treatment plan which results in the reduction is also referred to as non-simultaneous reduction treatment plan. The term "allowed" means for example that the non-simultaneous reduction treatment plan represents a potential candidate for a treatment plan to be determined by the treatment plan determining step and is not excluded as a potential candidate for a (optimised) treatment plan. According to an embodiment, the allowance results in the preference of the non-simultaneous reduction treatment plan compared to a simultaneous treatment plan (which results in higher exposure) since the dose criteria data request a low exposure of outside body parts to treatment radiation. According to another embodiment, the term "allowed" encompasses that the non-simultaneous reduction treatment plan is preferred over a simultaneous treatment plan which results in a higher exposure or it is an obligation (must) to choose a non-simultaneous reduction treatment plan instead of a simultaneous treatment plan (which results in higher exposure). For example the dose criteria data describe the criterion that one of potential treatment plans has to be determined which results in the lowest possible exposure of outside body parts to treatment radiation while the targets are exposed to at least the predetermined dose of treatment radiation. In this way, the allowance of determining a non-simultaneous treatment plan results in determining a non-simultaneous treatment plan instead of a simultaneous treatment plan if the non-simultaneous treatment plan is a non-simultaneous reduction treatment plan.

The aforementioned reduction is for example achieved compared to the case that all of the at least two target sets are subjected to the treatment radiation simultaneously during treatment time while for example both the simultaneous and the non-simultaneous treatment plan fulfil the criteria described by the dose criteria data. For example, the at least two target sets are subjected to the same or higher treatment radiation dose in the case of treatment in accordance with the non-simultaneous treatment plan than in case of treatment in accordance with the simultaneous treatment plan. The non-simultaneous and the simultaneous treatment plan is for example that one of the plurality of potential simultaneous treatment plans which best fulfils the dose criteria data, i.e. is for example an optimum simultaneous treatment plan. The radiation volume reduction criterion can be fulfilled by a simultaneous treatment plan if there is no non-simultaneous treatment plan which results in a reduction of the exposure, for example of healthy volume subjected to treatment radiation at least to a predetermined extent. The radiation volume reduction criterion can be fulfilled by a non-simultaneous treatment plan if the non-simultaneous treatment plan results in the reduction of the exposure, for example the healthy volume subjected to the treatment radiation at least to the predetermined extent. In other words, the radiation volume reduction criterion is deemed to be fulfilled by a non-simultaneous treatment plan if this non-simultaneous treatment plan results in the reduction of the exposure, for example the healthy volume subjected to treatment radiation at least to the predetermined extent. The radiation volume reduction criterion is deemed to be fulfilled by a simultaneous treatment plan, if there is no non-simultaneous treatment plan which results in the reduction of the exposure, for example of the healthy volume at least to the predetermined extent. A violation of the radiation volume reduction criterion means for example that the determined treatment plan is a simultaneous treatment plan although there is a non-simultaneous treatment plan which would result in less exposure, for example in less healthy volume subjected to treatment radiation (at least to the predetermined extent).

The non-simultaneous treatment plan describes treatment of not all of the targets for the whole treatment time. That is, one or more of the at least two target sets can be omitted during at least a time interval during treatment. Nevertheless, preferably each of the target sets is treated at least for one time interval during treatment time. Contrary to this, the simultaneous treatment plan describes simultaneous treatment of all of the targets for the whole treatment time. For example, the subjection of the healthy volume to treatment radiation is preferably reduced (for example has to be reduced) at least by a predetermined extent in order to fulfil the radiation reduction criterion. In other words, if the reduction would be less than the predetermined extent, then all of the targets are subjected simultaneously to radiation. Thus, the predetermined extent represents a threshold value which triggers switching between a simultaneous treatment plan and non-simultaneous treatment plan. The predetermined extent can be a predetermined percentage of dose reduction for the healthy volume compared to the case of simultaneous treatment of all of the at least two target sets in accordance with the treatment plan or can be a predetermined dose reduction of the dose absorbed by the healthy volume or can be a reduction of time, during which the healthy volume is subjected to the treatment radiation or can be a predetermined percentage defined by dividing the reduced volume by the total healthy volume, the reduced volume being the healthy volume which is avoided to be subjected to treatment radiation if switching from the simultaneous treatment plan to the non-simultaneous treatment plan. Of course further examples for defining the predetermined extent are possible. As mentioned above, the healthy volume can be defined to be the healthy volume in between all of the at least two target sets. The healthy volume can for instance be defined by a geometrical body which encompasses all of the at least two target sets and which is for example inside the patient's body, the geometrical body can for instance be a sphere or a cuboid and can for example be defined to be that one out of a plurality of possible geometrical bodies (of one or more types) which has the smallest volume but nevertheless encompasses all of the at least two targets. The healthy volume can also be defined to be the total volume inside the patient subjected to radiation with the exception of the volume occupied by the at least two targets.

The radiation volume reduction criterion is for example defined to request reduction of the healthy volume of the patient's body by determining a non-simultaneous treatment plan instead of a simultaneous treatment plan if the non-simultaneous treatment plan results in less exposure, for example less healthy volume subjected to treatment radiation at least to a predetermined extent than the simultaneous treatment plan. For example, if the non-simultaneous treatment plan results in less exposure, for example less healthy volume subjected to treatment radiation at least to a predetermined extent, then the at least one treatment beam cannot pass simultaneously through all of the at least two targets at least for a time interval during treatment in order to fulfil the radiation volume reduction criterion. For example, the radiation volume reduction criterion requests that a treatment plan (which is to be determined) describes a non-simultaneous treatment of the at least two target sets at least for a time interval during the treatment time if the treatment plan to be determined describes a non-simultaneous treatment according to which, for example at least to a predetermined extent, less exposure, for example less healthy volume of the patient's body is subjected to treatment radiation compared to the case of a treatment in accordance with another treatment plan which describes simultaneous treatment of the at least two targets during the treatment time.

The predetermined extent can be a combination of one of the aforementioned examples, further examples are possible. For example, the predetermined extent can be a function of the increase of treatment time which results from a non-simultaneous treatment plan (which describes the non-simultaneous treatment) compared to the simultaneous treatment plan (which describes the simultaneous treatment). For example, the required predetermined extent can be the higher the higher the increase of treatment time is if the non-simultaneous treatment plan is chosen instead of the simultaneous treatment plan. The simultaneous treatment plan is for example determined by reducing the amount of healthy volume subjected to treatment radiation as best as possible while still simultaneously treating all of the at least two targets. With respect to the minimization a reference is made to the article by Kang et al., A method for optimizing LINAC treatment geometry for volumetric modulated arc therapy of multiple brain metastases, Med. Phys. 37(8), August 2010, the entirety of which is incorporated by this reference.

The aforementioned volume reduction criterion is preferably described and for example represented by referring to the one or more sub-beams. For example, the aforementioned exposure, for example the amount of healthy volume subjected to radiation can be reduced and/or is deemed to be reduced if there is not more than one target treated by one of the sub-beams which is spatially separate to the other sub-beams. This means in more detail that, if viewed from the perspective of the spatially separate sub-beam, no spatially separate target sets should be covered by the spatially separate sub-beam but preferably just one target set is covered by the spatially separate sub-beam. In other words, if projecting the at least two target sets into a plane perpendicular to the (beam direction of the) spatially separate one of the one or more sub-beams and if projecting the cross section area of the spatially separate sub-beam into the same plane, then there preferably lies not more than one of the at least two projected spatially separated target sets spatially separate from each other within the projected cross sectional area. On the other hand, the exposure, for example the healthy volume subjected to treatment radiation is increased if the projected cross section covers two or more projected target sets which are spatially separate in the plane (referred to as "projection plane"). In this case, the volume between the two or more target sets is subjected to treatment radiation. The term "spatially separate sub-beam" means that the sub-beam is integral, for example has no contact to other sub-beams, for example the projected cross sectional area of the spatially separate sub-beam does not overlap with a projected cross sectional area of another sub-beam. For example if two or more sub-beams merge during treatment in accordance with the treatment plan, and this results in the aforementioned overlap, then the two or more sub-beams are treated to be one new spatially separate sub-beam. According to an embodiment, there is a defined minimum distance which the projected targets have to have in the projection plane in order to be considered to be "spatially separate" in the projection plane. This minimum distance can be a predetermined minimum distance which is for instance higher than 1 mm or 5 mm and less and 10 cm or 5 cm. This minimum distance can be a function of for example can correspond to the minimum distance which can be achieved by the treatment device, for example by the beam shaping device between two neighboring spatially separate sub-beams. For instance, in case a collimator is used for beam shaping, the minimum distance is for instance the distance caused between two sub-beams if just one leaf is in between the sub-beams or a function of this distance like this distance multiplied by a predetermined factor (which is for example higher than 0.1 or 0.3 and less than 3 or 10). In view of this, the aforementioned criterion is described for spatially separate sub-beams. Preferably, treatment plan is determined which allows for simultaneous treatment of all of the at least two targets during the treatment time (i.e. during the total treatment time). However, a non-simultaneous treatment of the at least two targets is allowed, for example preferred, for example has to be performed if the aforementioned criterion (of not more than one target within a cross sectional area of spatially separate sub-beam) cannot be fulfilled otherwise. As mentioned above, the reduction of subjection of healthy volume to treatment radiation should be at least to the above-mentioned predetermined extent in accordance with an embodiment. Applying this to the "not more than one target" criterion (see criterion a in preferred embodiment B), this means that not more than one target (for example at least for not for longer than a predetermined time) is treated by a spatially separate sub-beam according to an embodiment. In other words, the "not more than one target" criterion is considered to be only violated if more than one projected target is covered (continuously) by the projected cross sectional area of the spatially separate sub-beams for more than the predetermined time. Also this predetermined time can be a function of the extension of treatment time which can result from choosing the non-simultaneous treatment plan instead of a simultaneous treatment plan. The predetermined time can also be a fixed time which be zero or more, for example can be longer than 0.1 second or 1 second and which can be shorter than 10 seconds or one minute. The predetermined time can also be a percentage of the time of simultaneous treatment of two targets by one spatial separate sub-beam in accordance with the simultaneous treatment plan. The predetermined time can also be a function of the dose to be additionally absorbed by healthy volume until the predetermined time is reached compared to the case the predetermined is set zero.

If a non-simultaneous treatment plan is determined in order to fulfil the treatment beam criteria data, then not all of the target sets are treated simultaneously for the whole of the treatment time. For example, if no simultaneous treatment plan can be found which fulfils the radiation reduction criterion and/or, for example if there is a (candidate) non-simultaneous treatment plan which fulfils the radiation reduction criterion, for example then the target sets which are subjected to treatment at a specific time during treatment are preferably described by target set data. The positional information contained in the target set data can be function of time which time is within treatment time. The treatment plan is preferably determined based on the set of targets, that is according to an embodiment of the invention, the acquisition of the target sets can be a step before determination of the treatment plan or according to another embodiment of the invention, the target set is determined while determining the treatment plan (for instance by using interactive steps). The target set can be acquired by determining the target set such that each of the at least two target sets is treated at least for a time interval of the treatment time, for example so that each of the target sets is subjected to the required treatment dose required for one treatment session (which required dose is described by the above-mentioned dose criteria data which are for example comprised by the target beam criteria data).

As mentioned above, a simultaneous treatment plan is preferred. If this is not possible without violating the radiation reduction criterion, the number of target sets is preferably maximized (for example for any time during treatment time) for example in order to minimize the total treatment time. Preferably, the treatment beam criteria data describe this maximization criterion. Preferably, the treatment beam criteria data also describe that the treatment plan, for example the set of targets is determined so that the treatment time is minimized. This determination is preferably performed based on the target data, the treatment beam constraint data and the treatment beam criteria data. The treatment plan is preferably determined using optimisation algorithms which for example vary parameters of potential treatment beam arrangements (like beam positions and/or treatment time) and/or the set of targets (see below) in order to find the optimised treatment plan.

The treatment plan can be determined by generating a plurality of candidate treatment plans which describe potential treatment arrangements. Then, for each of the candidate treatment plans it is checked whether they fulfil the treatment beam criteria data. That one which fulfils the criteria best is selected as the determined treatment plan.

As mentioned above, the treatment plan can be determined based on the target set data which is determined before starting to determine the treatment plan. According to an embodiment, the target set is determined by determining a candidate target set. The target set is determined by omitting at least one set target from the candidate target set during a first time interval during the treatment time and by including the omitted targets into the another candidate target set during a second time interval outside the first time interval. Then it is checked whether a treatment plan can be determined for the candidate target set which fulfils the treatment beam constraints data and the treatment beam criteria data. If a treatment plan can be determined, then the determination of the treatment plan is achieved. If a treatment plan cannot be determined, a new target set is generated and the preceding steps are repeated by varying the time intervals and/or by varying the omitted targets.

The aforementioned omission of at least one target can be in accordance with a brute-force optimisation algorithm which varies all possible options in order to find the set of targets which best fulfils the treatment beam criteria. Alternatively, targets can be omitted during which the radiation reduction criterion and for example the "not more than one target" criterion is violated if treatment is performed in accordance with the simultaneous treatment plan. Thus, the simultaneous treatment plan which violates the "not more than one target criterion" can be used in order to identify the violation time interval and in order to identify those (more than one) targets (referred to as "violation targets") which are involved in the violation of this criterion, i.e. the spatially separate projections of which are covered by the projection of a cross section of one spatially separate sub-beam. Thus, according to an embodiment, preferably at least one of those violation targets is omitted for the violation time in order to find the candidate target set and at least one of the violation targets is for instance included in the set of targets as exclusive or non-exclusive member of the set after the non-omitted targets have been subjected to the treatment radiation for example in accordance with the dose criteria data describing the dose criteria for the non-omitted targets and/or for example before or after a change of the treatment path (e.g. the rotation of the patient; see below) has been performed.

The treatment device preferably comprises a treatment beam source (e.g. at least one of an outlet of a particle accelerator, an X-ray tube and radioisotope) which is movable relative to the at least two targets. Alternatively or additionally, the patient's body may be movable in a treatment setup comprising the patient's body and a patient support device (such as a patient bed and/or couch) and the treatment device, for example the patient support device may be movable. The movement of the treatment beam source is for example constrained in that it has to move along a path for example in order to deliver an arc of conformal radiation. For example, the only movement of the patient during treatment is a rotation of the patient. The relative position of the path relative to the patient can change e.g. by the aforementioned rotation. The path which can change its position relative to the patient and which is described in a reference system in which the at least two targets are at rest is referred to as "treatment path". Thus the treatment path can change due to movement of the patient. The path which is described in a reference system in which the treatment device is at rest is described as "device path". The device path does not change if the patient is moved. The path can have for example an arc shape, i.e. the beam sources moves along the arc. The movement is for example from a starting point to an end point in one direction and then from the end point back to the start point in opposite direction. Both of these movements are referred to as complete movements. The issue of radiation can be performed during the complete movement only when the beam source is within one or more sections of the path or for the (whole) path. The section can differ depending on forward movement or backward movement of the beam source. The aforementioned sub-treatment plans can for example describe the treatment for a section of the path or for the path (i.e. the full path). The sub-treatment plans are for example related to movements of the beam source where there is no change of direction of movements. Thus, for instance a first sub-treatment plan relates to an arc section of e.g. 0-30°, a second sub-treatment plan relates to a subsequent arc section of e.g. 30-60° and a third sub-treatment plan relates to a further subsequent arc section to e.g. 60-90° and a fourth arc section relates to a backward movement of the beam source along an arc section from e.g. 60° to 30°. While for instance the first and third sub-treatment plans include all of the at least two target sets, the second sub-treatment plan omits one or more of all of the at least two target sets. By the omission, the second sub-treatment plan can fulfil the radiation reduction criterion. Then, for instance the fourth sub-treatment plan describes treatment of the omitted one or more target sets in order to complete treatment of all targets. By omitting target sets during a forward movement along a path and by treating omitted targets during a backward movement along the same path, the treatment time can be minimized. The aforementioned arc sections represent just examples.

According to an embodiment, the target sets are assigned to one path (i.e. the full path from a starting point of the device path to an end point of the device path). Thus, the beam source moves along the device path in order to treat one of the target sets and repeats such a (for instance forward or backward) movement until all target sets are treated which means that all of the targets of the at least two targets have been treated. For instance, during a first movement along the device path, a first subset is treated. Then, during a second movement of the device path, a second subset is treated which includes as many as possible of the targets omitted from the first target set while still complying with the radiation reduction criterion. If necessary, a third target set or more target sets are treated during subsequent movements of the beam source along the device path in order to finally treat all targets. Preferably a change of the treatment path (e.g. by rotation of the patient) is only performed after all of the target sets of the at least two target sets have been treated at least for a time interval, in other words only after each of the at least two target sets was a member of one of the treated target sets.

A section of a path where a target set is omitted are referred to herein as omitting section and a section of a path where the omitted target set is treated are referred herein as supplementing section. According to an embodiment, the omitting section is described by a sub-treatment plan which describes a treatment by moving the beam source in a first direction (e.g. forward) and a supplementing section is described by a sub-treatment plan which describes a treatment by moving the beam source in a second direction (e.g. backward). The terms backward moving and forward moving are freely exchangeable herein. The first and second direction can be the same or can be different, for example opposite. According to a particular embodiment, the omitting section and the supplementing section differ from each other if those sections belong to the same treatment path. According to another embodiment, there are different treatment paths for a forward movement and a backward movement of the beam source. For example, the different treatment paths are realized by a movement of the at least two target sets (i.e. of the patient's body) in a reference system in which a first path along which the beam source moves is at rest. The movement is for example a rotational movement. For instance, the beam source is moved along an arc of the device path which describes the first treatment path. Then the patient is rotated. Then the beam source moves backward along the same arc of the same device path but due to the rotation of the patient, the second treatment path differs from the first path. The term treatment path relates to a relative position between the patient and the at least two target sets. Thus, the position of the arc of the device path in a reference system in which the treatment device is at rest does not change while the position of the corresponding treatment path (e.g. arc) in a reference system in which the patient is at rest changes due to the rotation of the patient in the reference system in which the treatment device is at rest. Preferably, in this case, the omitting section and the supplementing section would be the same if there were no relative movement of the at least two targets in the reference system in which the treatment device is at rest, i.e. in which the one or more possible device paths are at rest. For example, due to the rotation of the patient different directions of incidence of the sub-beam are possible which allow to fulfil the treatment beam criteria data. It is just an option that the omitting section and the supplementing section are identical sections of the device path, they can of course also be different. For example, the end point of the first treatment path is preferably identical with the starting point of the second treatment path in order to reduce the treatment time.

For example, the determination of one of the subsets and/or one of the sub-treatment plans depends on other already determined sub-sets and/or sub-treatment plans used for the determination of the treatment plan in order to stepwise determine the sub-sets and finally the set of target sets.

Since, as already mentioned above, beam generation is subjected to certain technical constraints, certain arrangements of targets cannot be treated with certain configurations of a treatment beam source and a beam shaping device. For example, if at least two of the at least two target sets are located in a direction parallel to the movement direction of the leafs of a multi-leaf collimator, it can be not possible to direct sub-beams to each of the targets without directing at least part of the sub-beam to healthy volume located between the at least two target sets. However, such situations should be avoided as far as possible so as to keep the exposure to radiation for the patient as low as possible.

In other words, each defined, particularly vertical plane comprises at least one target set which is determined by the method steps described above. Determining the at least one target set for a plane can depend or can be independent from the determination for at least one subset of targets determined for another plane. For example, the target set data can describe not only one but a plurality of target sets, which is also called set of target sets.

If the beam source is moved along a straight line, or preferably along an arc-shaped pathway, and if preferably the patient support device is additionally moved, a certain time interval relates to a certain sector or angle which is covered by the beam source during this time.

Therefore, a target set is omitted during a certain time interval of treatment, it can be said that this target is omitted for a certain treatment distance or treatment-angle. In other words and according to this preferred embodiment of the present invention, only treatment angles are considered for which at least one target has been omitted for a foregoing plane. For example, if a target is omitted for a certain distance or angle in a plane, only this distance or angle will be covered by the beam source in a following plane. This allows for further reduction of treatment time, since the beam source only covers the considered distance or angle in plane, for which angle or distance a target has been omitted in a foregoing plane, particularly the directly foregoing plane.

According to a further preferred embodiment, control data is provided comprising information on the at least one determined treatment beam arrangement and/or the at least determined set of at least two targets for at least one plane, particularly, comprising information to successively treat at least one determined set of targets of at least one plane by means of the at least one respectively determined treatment beam arrangement. In other words, control data is determined based on the determined treatment plan (treatment beam arrangement) for simultaneous treatment of a set of at least two targets by the arrangement. This control data is configured to generate control signals for controlling at least one of a couch and a treatment device comprising a beam shaping device and beam source as described further below. More generally spoken, control data is configured to generate control signals for controlling any device which directs a beam which may comprise at least two sub-beams to a target, move the beam relatively to the target and shape the cross-sectional area of the beam accordingly.

A further aspect of the present invention refers to a radiation therapy system, comprising the aforementioned computer, a patient support device supporting a patient, and a treatment device comprising the beam shaping device and the beam source, wherein the treatment device and the patient support device are movable relatively to each other, particularly wherein the patient support device is at least one of rotatable and translatable in a horizontal plane and/or the treatment device is movable along an arc-shaped pathway lying in a specifically vertically oriented plane.

The invention also relates to a program which, when running on a computer or when loaded onto a computer, causes the computer to perform one or more or all of the method steps described herein and/or to a program storage medium on which the program is stored (for example in a non-transitory form) and/or to a computer on which the program is running or into the memory of which the program is loaded and/or to a (physical, for example electrical, for example technically generated) signal wave, for example a digital signal wave, carrying information which represents the program, for example the aforementioned program, which for example comprises code means which are adapted to perform any or all of the method steps described herein.

The present invention is also directed to a radiotherapy system as mentioned in the claims.

The invention is furthermore directed to the following preferred embodiments:

A. A data processing method for determining a treatment plan for radiation therapy treatment of at least two spatially separate targets by means of a treatment device constituted to treat the at least two targets by means of one or more sub-beams during a treatment time, the one or more sub-beams constituting at least one treatment beam which is to pass through the at least two targets in accordance with a treatment plan during the treatment time, the treatment device being further constituted to allow for simultaneous treatment of the at least two targets by at least two of the sub-beams at least during a time interval during the treatment time, the method comprising the following steps performed by a computer:
 acquiring target data describing spatial information on the at least two spatially separate targets in a patient's body;
 acquiring treatment beam constraint data which allow determination of potential treatment plans which can be realized by the treatment device and which potential treatment plans describe potential arrangements of the at least one treatment beam, referred to as potential treatment beam arrangements;
 acquiring treatment beam criteria data describing criteria for the treatment of the at least two targets by the at least one treatment beam, the criteria comprising a radiation reduction criterion which describes that a treatment plan is allowed to be determined which describes a non-simultaneous treatment of the at least two targets at least for a time interval during the treatment time if this treatment plan describes that parts of the patient's body outside the at least two targets are less exposed to treatment radiation, for example at least to a predetermined extent, compared to the case of a treatment plan which describes a simultaneous treatment of the at least two targets during the treatment time; and
 determining the treatment plan which fulfils the radiation reduction criterion based on the target data, the treatment beam constraint data and the treatment beam criteria data.

B. The method of the preceding embodiment, wherein the radiation reduction criterion comprises the following criteria a) and b), for example is represented by the following criteria a) and b):
 a) the criterion a) describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, for example by at least a predetermined distance, within the projected cross sectional area, for example at least for not longer than a predetermined time; and
 b) the criterion b) allowing that the treatment plan describes that the at least one treatment beam does not pass simultaneously through all of the at least two targets at least for a time interval during treatment in order to fulfil the criteria a), wherein for example this is only allowed if this results in a reduction of the exposure of the parts of the patient's body outside the at least two targets at least to the predetermined extent.

C. The method according to the preceding embodiment, wherein, for example if no treatment plan can be determined which describes the simultaneous treatment and fulfils the radiation reduction criterion, for example if the at least one treatment beam cannot pass simultaneously through all of the at least two targets during treatment in order to fulfil the radiation reduction criterion, for example then the treatment plan is determined based on a set of targets, the set of targets describing targets selected out of the at least two targets for the simultaneous treatment by the at least one treatment beam as a function of time and wherein each of the at least two targets is selected at least for a time interval of the treatment time and wherein at least for a time interval during treatment time not all of the at least two targets are selected.

C. The method of the preceding embodiment, wherein the number of the targets in the set of targets is maximized for determining the treatment plan based on the target data, the treatment beam constraint data and the treatment beam criteria data.

D. The method of one of the two preceding embodiment, wherein the set of targets is determined so that the treatment time is minimized based on the target data, the treatment beam constraint data and the treatment beam criteria data.

E. The method of one of the preceding embodiments as far as depending on embodiment C, wherein the set of targets is determined by determining a candidate target set, the candidate target set being determined by omitting one or more of the at least two targets during a first time interval during the treatment time, by including the omitted one or more of the at least two targets into the candidate target set during a second time interval outside the first time interval and during the treatment time and by determining whether the treatment plan can be determined for the candidate target set and by determining the candidate target set to be the set of targets if the treatment plan can be determined.

F. The method of the preceding embodiment, wherein the candidate target set is determined by omitting one or more of the at least two targets during a time interval during which a potential treatment plan violates the volume reduction criterion, for example the criterion a) of claim 2, the potential treatment plan fulfilling the condition that all of the at least two targets are simultaneously treated all over the treatment time, the time interval being referred to as violation time interval, and by including the omitted one or more of the at least two targets into the candidate target set during a time interval outside the violation time interval and inside the treatment time.

G. The method of one of the preceding embodiments, wherein the treatment plan is determined by combining sub-treatment plans which are to be performed one after the other during treatment time and which respectively describe treatment of a sub-set of the at least two targets, the sub-treatment plans being determined based on the spatial information on the targets of the respective sub-set, the treatment beam constraint data and the treatment beam criteria data, the sub-sets being selected so that each of the targets being included in at least one of the subsets and the sub-treatment plans fulfilling the volume reduction criterion, for example the criterion a) of claim 2 for all the targets of the sub-set.

H. The method of the preceding embodiment, wherein the treatment beam criteria data comprise that all targets of each subset are treated at least sequentially and preferably simultaneously in accordance with the respective sub-treatment plan during a sub-treatment time interval.

I. The method of the preceding embodiment, wherein the sub-sets are determined based on candidate sub-sets, and those one of the candidate sub-sets are selected as subset for which a sub-treatment plan can be determined which describes simultaneous treatment of all targets of the subset during the whole sub-treatment time while not violating the radiation reduction criterion.

J. The method of one of the preceding embodiments as far as depending from embodiment G, wherein the treatment device comprises a beam source to issue the at least one treatment beam and wherein there is a path of movement of the beam source relative to the at least two targets referred to as treatment path, which is for example a preferably arc-shaped relative movement of the beam source in at least one vertical plane relative to the at least two targets, the sub-treatment plans describing treatment during movement of the beam source along the treatment path and/or a section of the treatment path,
  a) wherein there is more than one complete movement of the beam source along the treatment path between a starting point and an end point and wherein the treatment of each of the subsets is respectively assigned to one of the complete movements so that by performing more than one complete movement all targets are treated, and for example wherein the treatment plan is determined so that the treatment path is only changed by rotating the patient in a reference system in which the treatment device is at rest, for example by rotating the plane, if and after all of the at least two targets have been treated,
  b) wherein targets omitted according to one of the sub-treatment plans during forward movement of the beam source along a first subsection of the treatment path are treated according to another sub-treatment plan during backward movement or during another forward movement along a second subsection of the treatment path which first subsection can be identical; and/or
  c) wherein targets omitted according to one of the sub-treatment plans during movement of the beam source along a first subsection of a first treatment path are treated according to another sub-treatment plan during movement along a second subsection of a second treatment path, wherein the first treatment path and the second treatment path are for example different due to a movement of the patient in a reference system in which the treatment device is at rest, for example by rotating the at least two targets relative to the vertical plane, wherein for example the first and second subsection would be identical without the movement of the patient in the reference system.

K. The method according to one of the preceding embodiments, wherein the treatment plan which describes simultaneous treatment and which is used for the definition of the radiation reduction criterion is a treatment plan which has been determined by minimizing the healthy volume which is subjected to treatment radiation.

L. A program which, when running on a computer or when loaded onto a computer, causes the computer to perform the method according to any one of the preceding embodiments and/or to a program storage medium on which the program is for example non-transitory stored and/or a computer on which the program is running or into the memory of which the program is loaded and/or a signal wave, for example a digital signal wave, carrying information which represents the program, for example, the aforementioned program for example comprises code means adapted to perform all the steps of the method of one of the preceding embodiments.

M. A radiation therapy system, comprising:
  the computer of the preceding embodiment;
  a patient support device for supporting a patient;
  and a treatment device comprising the beam shaping device (4) and the beam source.

N. The radiation therapy system of the preceding embodiment, wherein the treatment device and the patient support device are movable relatively to each other, particularly wherein the patient support device is at least one of rotatable in a horizontal plane and/or the treatment device is movable along an arc-shaped pathway lying in a specifically vertically oriented plane.

DEFINITIONS

In this section, definitions for specific terminology used in this disclosure are offered which also form part of the present disclosure.

The method in accordance with the invention is for example a data processing method. The data processing method is preferably performed using technical means, for example a computer. The data processing method is preferably constituted to be executed by or on a computer, for example it is executed by or on the computer. In particular, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows to display information outputted by the computer e.g. to a user. An example of a display device is an augmented reality device (also called augmented reality glasses) which may be used as goggles for navigating. A specific example of such augmented reality glasses is Google Glass (trademark of Google Inc.). An augmented reality device may be used to both input information into the computer by user interaction and to display information outputted by that computer.

Preferably, the inventive method is at least partly executed by a computer. That is, all steps or just some of the steps (i.e. less than a total number of steps) of the inventive method may be executed by a computer.

The expression "acquiring data" for example encompasses (within the framework of a data processing method) the scenario in which the data are determined by the data processing method or program. Determining data for example encompasses measuring physical quantities and transforming the measured values into data, for example digital data and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). A computer herein is a technical computer which comprises for example technical, for example tangible components, for example mechanical and/or electronic components. Any device mentioned herein is a technical, for example tangible device.

The present invention relates to the field of medicine and for example to the use of beams, for example radiation beams, to treat parts of a patient's body, which are therefore also referred to as treatment beams. A treatment beam treats body parts which are to be treated and which are referred to in the following as "treatment body parts" and/or "target" and/or "irradiation target" with each equal meaning. These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, for example in the field of oncology. For treating cancer for example, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

DESCRIPTION OF THE FIGURES

In the following, an example embodiment of the present invention is described with reference to the figures. The example embodiment is to be regarded as merely an example of the invention without limiting the invention to the example embodiment.

Figure 1:
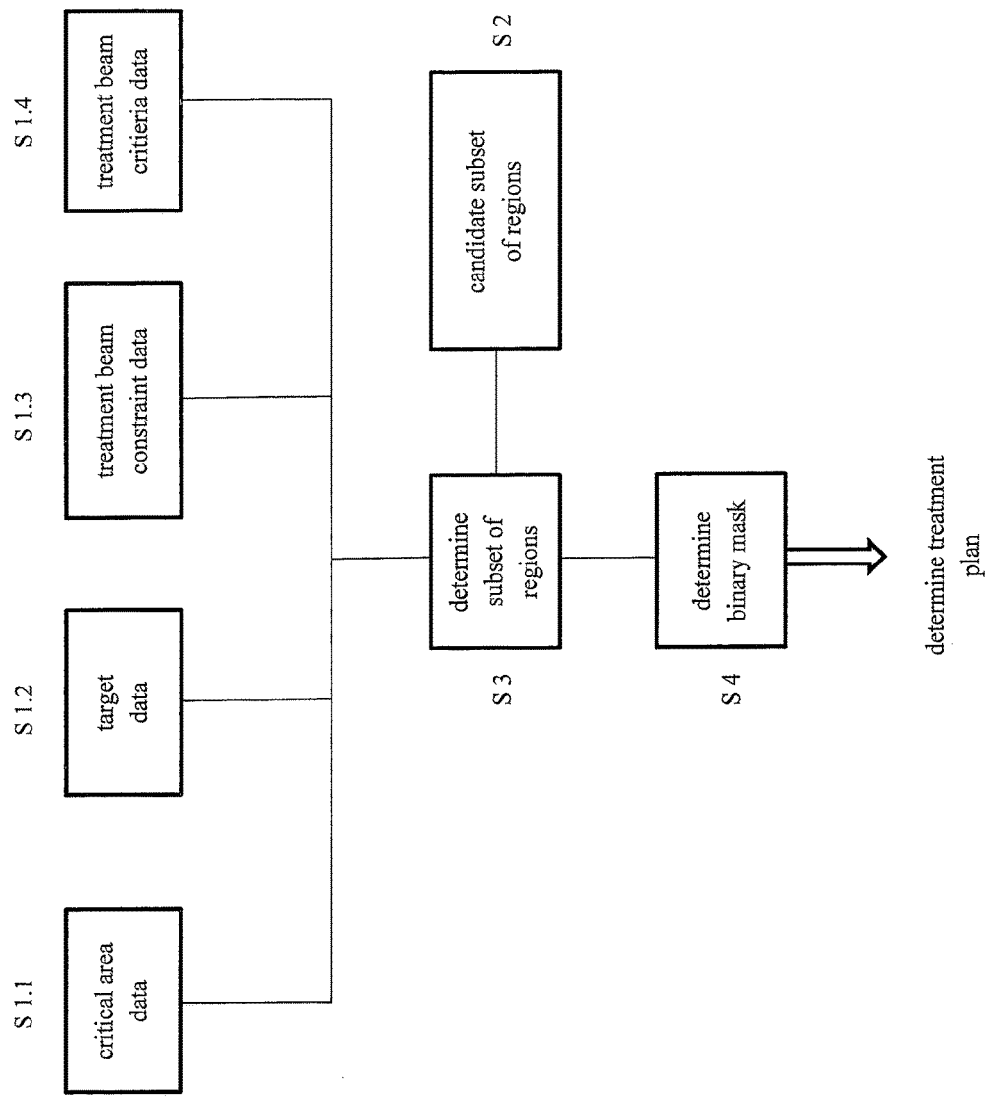
FIG. 1 shows an exemplary flow diagram of the data processing method of determining a target set.

As can be seen in FIG. 1 critical area data, target data, treatment beam constraint data and treatment beam criteria data are acquired in steps S1.1, S1.2, S1.3 and S1.4, respectively, as constraints for determining a constraint mask in step S4 which embodies the target set data. The target data describes spatial information (for example the positions) of the targets 10 to be treated in a patient's body, treatment beam constraint data describes possible treatment beam arrangements and treatment beam criteria data describes criteria for the treatment of the targets. If it is not possible to treat all targets 10 by one treatment beam arrangements without violating treatment-criteria, one or more of the targets 10' causative for the violation are omitted from the candidate subset of targets 10, thereby obtaining a set 11 of targets 10 (i.e. set targets 10, the subset 11 embodying the above-described target set) comprising targets 10 which can be treated simultaneously by a given treatment beam arrangements so that a sub-treatment-plan can be determined for treatment of the set targets 10. Since the omitted target 10' will not be treated together with the previously determined target set 11, at least one further subset of targets is preferably determined containing the omitted target(s) 10', wherein a further sub-treatment-plans can be determined for the further subset containing the omitted target(s) 10'.

By combining the determined sub-treatment-plans, a treatment plan for all targets is determined.

Figure 2:
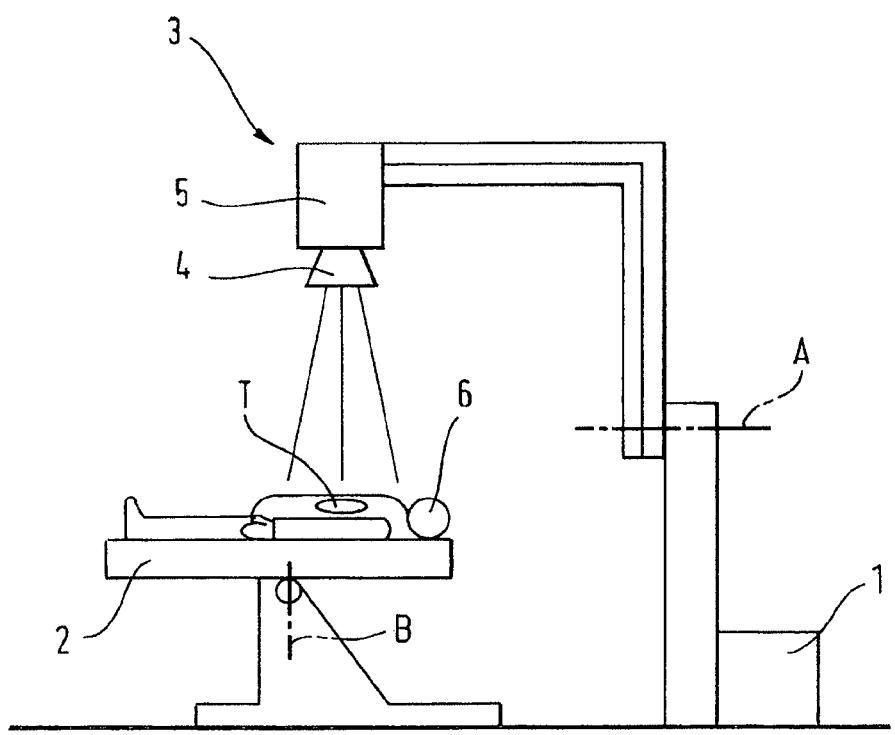
FIG. 2 shows an exemplary embodiment of a radiation therapy system in accordance with the present invention.

FIG. 2 shows an embodiment of the inventive radiation therapy system comprising a computer 1 on which a program is loaded which causes the computer to perform the inventive method, particularly to control the treatment device 3 comprising a beam shaping device 4 and a beam source 5, and a couch 2 on which a patient 6 is placed.

It can be seen from FIG. 2 that the treatment device 3 can be moved in a vertical plane (or, more general, within a section of a spherical surface) along an arc-shaped path of movement around an axis A so as to move around the patient 6 lying on a couch 2. Furthermore, the couch 2 is at least one of rotatable and translatable at least in the horizontal plane and preferably also in the other two spatial dimensions which run for example rectangular to the horizontal plane.

The beam source 5 generates a radiation beam comprising at least two sub-beams directed to a plurality of targets T in the body of the patient 6. The cross-sectional area of the beam/sub-beams is formed by the beam shaping device 4 for example so that each sub-beam is assigned for treatment of one (or more) of the targets T. The treatment device 3 is moved along a predefined distance on its path of movement around the patient, while the beam source 5 generates a beam for treating targets T. After a first subset of targets is treated by the beam, a second and further subsets of targets T may be treated by a beam. According to an embodiment, after all targets T have been treated by the beam, the couch 2 is rotated around axis B so as to change the relative position between the patient 6 and the treatment device 3. This is referred to herein as determining a new plane for the treatment device. According to another embodiment, the rotation of the couch is performed before all targets are treated and in the at least one further plane, targets can be treated which have not been treated in the forgoing planes.

Figure 3:
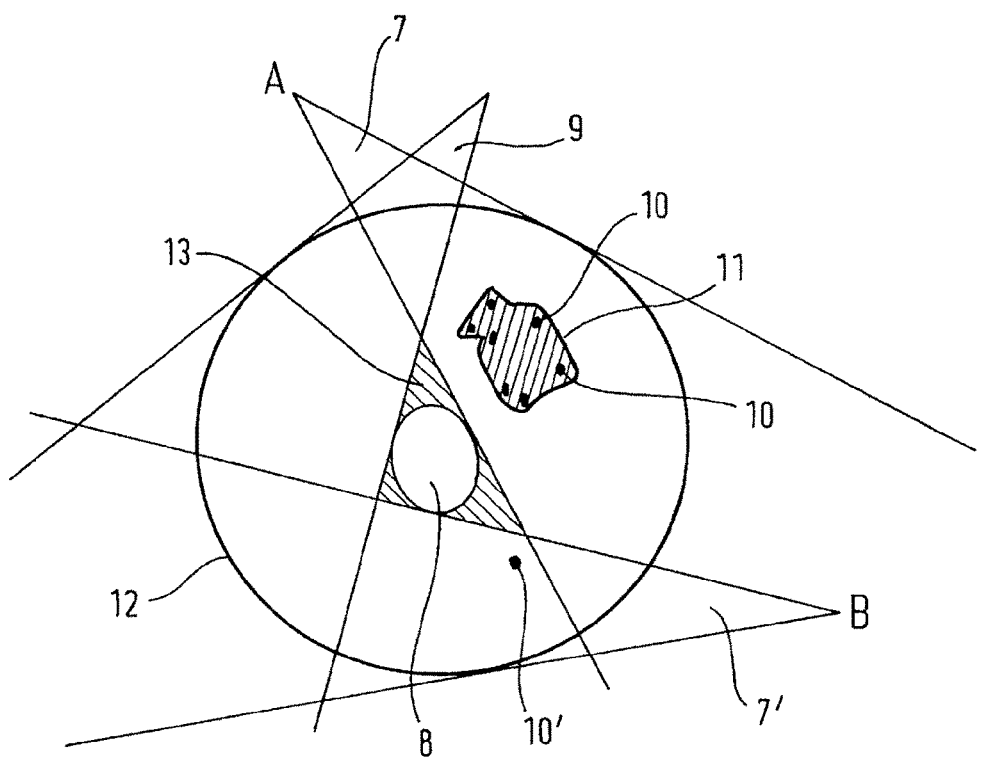
FIG. 3 shows omission of a risk region defining angular intervals for permitted beam directions.

FIG. 3 illustrates how an angular irradiation regions (angular intervals) 7 is defined in which irradiation of a planning target volume represented by an anatomical body part 12 (representing a planning target volume embodied by an anatomical structure, for example the prostate) is permitted (and preferably enforced during later generation of a radiation therapy treatment plan). The angular region 7 comprises a target set 11 comprising irradiation targets 10 embodying the set targets. The irradiation target 10' represents an omitted target which cannot be irradiated simultaneously with the set targets 10 within irradiation region 7 since irradiation of the risk region 8 should be avoided. Due to the arrangement of treatment beams and the geometry of the irradiation regions 7, 7', an omitted region 13 remains around the risk region 8 which cannot be irradiated if irradiation of the risk region 8 is to be avoided. A further irradiation region 7' is defined in which the omitted target 10' lies so that the omitted target 7 can be irradiated sequentially before or after irradiation of the set targets 10. To this end, the position of the treatment device 3 relative to the anatomical body art 12 has to be changed from position A to position B or vice versa, respectively. Furthermore, angular interval 9 represents a non-irradiation region because there are no irradiation targets 10, 10' in that region. A non-irradiation region 9 is an angular interval in which irradiation of the anatomical body part 12 is suppressed during later generation of a radiation therapy treatment plan. Regions 7, 7' and 9 constitute a subset a candidate subset of regions about which information (for example positional information) is acquired in step S2 and for which it is determined in the basis of the data acquired in steps S1.1 to S1.4 whether they shall a member of the subset of regions (i.e. irradiation regions) determined in step S3. Ideally, as much of the anatomical body part 12 as possible shall be irradiated while avoiding irradiation of the risk region 8. For example, the entire area of the anatomical body part 12 should be covered by irradiation regions 7, 7', and the number of non-irradiation regions 9 shall be zero. For example, a corresponding number of fan-shaped irradiation regions 7, 7' would be distributed over the area of the anatomical body part 12 which surrounds the risk region 8. The fan shape of the regions 7, 7' and 9 is in principle due to the fan shape of the treatment radiation beam. However, the fan shape of the regions 7, 7' and 9 is not a required feature of the invention and the regions 7, 7' and 9 may take any other geometry depending on the beam geometry. As also shown in FIG. 1, the constraint mask which is described by the target set data is determined in step S4 on the basis of the subset of irradiation regions determined in step S3. The constraint mask prescribes for the subsequent generation of a radiation therapy treatment plan which parts of the anatomical body part 12 are to be determined as lying within an irradiation region and which are to be determined as non-irradiation regions, i.e. which parts of the anatomical body part 12 shall be designated for irradiation and which not.

Figure 4:
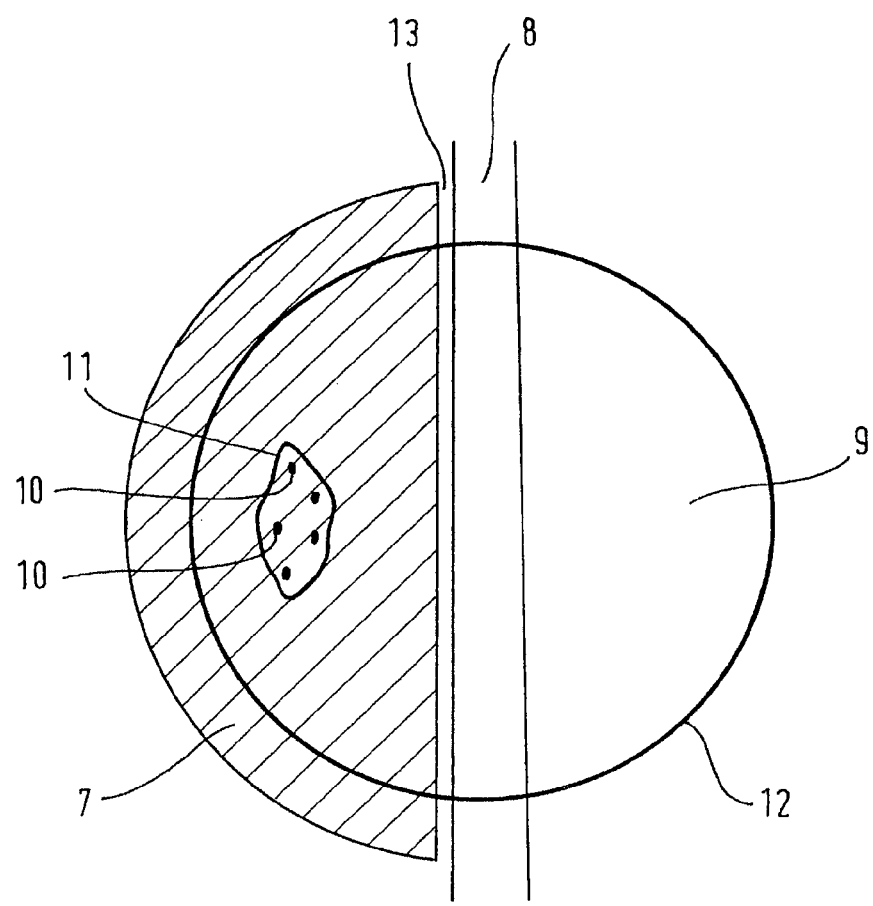
FIG. 4 shows the principle of defining a target volume.

FIG. 4 shows the division of a prostate 12 into an irradiation region 7 and a non-irradiation region 9 from a different perspective along a longitudinal cross-section of the urinary tract embodying a risk region 8. Otherwise, the same reference signs denote the same features as in FIG. 3. The features of the exemplary embodiment, for example the method steps, described with regard to FIG. 3 are therefore equally applicable to FIG. 4. As illustrated by FIG. 4, the spatial extent of an irradiation region 7 defined by the mask shown in FIG. 4 is preferably larger than the spatial extent of the anatomical body part 12.

The invention claimed is:

1. A radiation therapy system, comprising:
at least one computer comprising at least one processor and at least one memory, wherein a program is running on the at least one processor or loaded into the at least one memory which, when executed by the at least one computer, causes the at least one computer to determine a target set comprising at least one irradiation target in a patient's body for radiation therapy treatment by means of a treatment device constituted to treat the at least one target by means of one or more sub-beams, the one or more sub-beams constituting at least one treatment beam which is to pass through the at least one target in accordance with a treatment plan during the treatment time, the system operable to:
acquire, at a processor, critical area data describing spatial information on anatomical regions, irradiation of which regions is to be avoided during radiation therapy treatment;
acquire, at a processor, target data describing spatial information on the at least one irradiation target;
acquire, at a processor, treatment beam constraint data which allows determination of potential treatment beam arrangements which can be realized by the treatment device and which potential treatment beam arrangements describe potential arrangements of the at least one treatment beam;
acquire, at a processor, treatment beam criteria data describing criteria for the treatment of the at least one target by the at least one treatment beam, the criteria comprising a radiation reduction criterion which describes that a treatment plan is allowed to be determined which describes radiation treatment of the at least one target if this treatment plan describes that parts of the patient's body outside the at least one target, referred to as outside body parts, are less exposed to treatment radiation at least to a predetermined extent in the case of subsequent radiation therapy treatment of the at least one target and the outside body parts, compared to the case of a treatment plan which describes a simultaneous treatment of the at least one target and the outside body parts; and determine, by a processor and based on the critical area data and the target data and the treatment beam constraint data and the treatment beam criteria data, target set data describing a set of irradiation targets and spatial information on at least one irradiation region, wherein the target set data is determined, by a processor, based on at least one of information about the spatial relationship between the at least one irradiation target and the nearest neighbouring irradiation target and information about the envisaged radiotherapy treatment;

the radiation therapy system further comprising a couch for placing a patient;

a treatment device including a beam shaping device and a beam source, the treatment device being operably coupled to the computer for control of the treatment device by the computer.

2. The radiation therapy system of claim 1, wherein the treatment device and the couch are movable relative to each other.

3. A computer implemented method for determining a target set comprising at least one irradiation target in a patient's body for radiation therapy treatment by means of a treatment device constituted to treat the at least one target by means of one or more sub-beams, the one or more sub-beams constituting at least one treatment beam which is to pass through the at least one target in accordance with a treatment plan during the treatment time, the method comprising executing, on at least one processor of at least one computer, steps of:

acquiring, at a processor, critical area data describing spatial information on anatomical regions, irradiation of which regions is to be avoided during radiation therapy treatment;

acquiring, at a processor, target data describing spatial information on the at least one irradiation target;

acquiring, at a processor, treatment beam constraint data which allows determination of potential treatment beam arrangements which can be realized by the treatment device and which potential treatment beam arrangements describe potential arrangements of the at least one treatment beam;

acquiring, at a processor, treatment beam criteria data describing criteria for the treatment of the at least one target by the at least one treatment beam, the criteria comprising a radiation reduction criterion which describes that a treatment plan is allowed to be determined which describes radiation treatment of the at least one target if this treatment plan describes that parts of the patient's body outside the at least one target, referred to as outside body parts, are less exposed to treatment radiation at least to a predetermined extent in the case of subsequent radiation therapy treatment of the at least one target and the outside body parts, compared to the case of a treatment plan which describes a simultaneous treatment of the at least one target and the outside body parts; and determining, by a processor and based on the critical area data and the target data and the treatment beam constraint data and the treatment beam criteria data, target set data describing a set of irradiation targets and spatial information on at least one irradiation region, wherein the target set data is determined, by a processor, based on at least one of information about the spatial relationship between the at least one irradiation target and the nearest neighbouring irradiation target and information about the envisaged radiotherapy treatment.

4. The method of claim 3, wherein the number of the targets in the target set is maximized for determining the treatment plan based on the target data, the treatment beam constraint data and the treatment beam criteria data.

5. The method of claim 3, wherein the target set data is determined, by a processor, so that the treatment time is minimized based on the target data and the treatment beam constraint data and the treatment beam criteria data.

6. A method of determining a radiation therapy treatment plan, wherein the treatment plan is determined by a processor of a computer based on the target set data after execution of the method according to claim 3, and wherein the treatment plan fulfils is the radiation reduction criterion based on the target data and the treatment beam constraint data and the treatment beam criteria data.

7. The method of claim 6, wherein the treatment plan is determined, by a processor, by combining sub-treatment plans which are to be performed One after the other during treatment time and which respectively describe treatment of at least two target sets, the sub-treatment plans being determined, by a processor, based on the spatial information on the targets of the respective target set and the treatment beam constraint data and the treatment beam criteria data, the target sets being selected, by a processor, so that each of the targets being included in at least one of the target sets and the sub-treatment plans fulfilling a volume reduction criterion.

8. The method of claim 3, wherein the target set data is determined, by a processor, by determining, a candidate target set, the candidate target set being determined, by a processor, by omitting one or more of the at least two targets during a first time interval during the treatment time, by including, by a processor, the omitted one or more of the at least two targets into the candidate target set during a second time interval outside the first time interval and during the treatment time and by determining, by a processor, whether a treatment plan can be determined for the candidate target set and by determining, by a processor, the candidate target set to be the target set if it is determined, by a processor, that a treatment plan can be determined.

9. The method of claim 8, wherein the candidate target set is determined, by a processor, by omitting one or more of the at least two targets during a time interval during which a potential treatment plan violates the volume reduction criterion, the potential treatment plan fulfilling the condition that all of the at least two targets are simultaneously treated all over the treatment time, the time interval being referred to as violation time interval, and by including, by a processor, the omitted one or more of the at least two targets into the candidate target set during a time interval outside the violation time interval and inside the treatment time.

10. The method of claim 9, wherein the treatment beam criteria data comprises that all targets of each subset are treated at least sequentially and simultaneously in accordance with the respective sub-treatment plan during a sub-treatment time interval.

11. The method of claim 10, wherein the target sets are determined, by a processor, based on candidate target sets, and those of the candidate target sets are selected, by a processor, as subset for which a sub-treatment plan can be determined which describe simultaneous treatment of all targets of the respective target set during the whole sub-treatment time while not violating the radiation reduction criterion.

12. The method of claim 8, wherein the treatment device comprises a beam source to issue the at least one treatment beam and wherein there is a path of movement of the beam source relative to the at least two targets referred to as treatment path, which is an arc-shaped relative movement of the beam source relative to the at least two targets, the sub-treatment plans describing treatment during movement of the beam source along at least one of the treatment path and a section of the treatment path, wherein there is more than one complete movement of the beam source along the treatment path between a starting point and an end point and wherein the treatment of each of the subsets is respectively assigned to one of the complete movements so that by performing more than one complete movement all targets are treated, and wherein the treatment plan is determined so that the treatment path is only changed by rotating the patient in a reference system in which the treatment device is at rest, if and after all of the at least two targets have been treated, the method comprising at least one of the following features b) and c):

wherein targets omitted according to one of the sub-treatment plans during forward movement of the beam source along a first subsection of the treatment path are treated according to another sub-treatment plan during backward movement or during another forward movement along a second subsection of the treatment path which first subsection can be identical;

wherein targets omitted according to one of the sub-treatment plans during movement of the beam source along a first subsection of a first treatment path are treated according to another sub-treatment plan during movement along a second subsection of a second treatment path, wherein the first treatment path and the second treatment path are different due to a movement of the patient in a reference system in which the treatment device is at rest, wherein the first and second subsection would be identical without the movement of the patient in the reference system.

13. A non-transitory computer-readable program storage medium on which a program is stored which, when executed by at least one processor of at least one computer or loaded into at least one memory of at least one computer, causes the at least one computer to perform the following operations: determine a target set comprising at least one irradiation target in a patient's body fibs radiation therapy treatment by means of a treatment device constituted to treat the at least one target by means of one or more sub-beams, the one or more sub-beams constituting at least one treatment beam which is to pass through the at least one target in accordance with a treatment plan during the treatment time, the program when executed by the at least one processor causes the computer to perform the following operations:

acquire, at a processor, critical area data describing spatial information on anatomical regions, irradiation of which regions is to be avoided during radiation therapy treatment;

acquire, at a processor, target data describing spatial information on the at least one irradiation target;

acquire, at a processor, treatment beam constraint data which allows determination of potential treatment beam arrangements which can be realized by the treatment device and which potential treatment beam arrangements describe potential arrangements of the at least one treatment beam;

acquire, at a processor, treatment beam criteria data describing criteria the treatment of the at least one target by the at least one treatment beam, the criteria comprising a radiation reduction criterion which describes that a treatment plan is allowed to be determined which describes radiation treatment of the at least one target if this treatment plan describes that parts of the patient's body outside the at least one target, referred to as outside body parts, are less exposed to treatment radiation at least to a predetermined extent in the case of subsequent radiation therapy treatment of the at least one target and the outside body parts, compared to the case of a treatment plan which describes a simultaneous treatment of the at least one target and the outside body parts; and determine, by a processor and based on the critical area data and the target data and the treatment beam constraint data and the treatment beam criteria data, target set data describing a set of irradiation targets and spatial information on at least one irradiation region, wherein the target set data is determined, by a processor, based on at least one of information about the spatial relationship between the at least one irradiation target and the nearest neighbouring irradiation target and information about the envisaged radiotherapy treatment.

14. A computer comprising the non-transitory computer-readable program storage medium of claim 13.

15. A radiation therapy system, comprising:

at least one processor and associated memory having instructions which, when executed by the at least one processor, causes the at least one processor to determine a set of treatments targets in a patient's body for radiation therapy by a treatment device by one or more sub-beams, the instructions operable to:

acquire, by the at least one processor, critical area data describing spatial information on anatomical regions, irradiation of which regions is to be avoided during radiation therapy treatment;

acquire, by the at least one processor, target data describing spatial information on the at least one irradiation target;

acquire, by the at least one processor, treatment beam constraint data which allows determination of treatment beam arrangements emitted by the treatment device and which treatment beam arrangements describe arrangements of the at least one treatment beam;

acquire, at a processor, treatment beam criteria data, the criteria data comprising a radiation reduction criterion which describes radiation treatment of the at least one target if this treatment plan describes that parts of the patient's body outside the at least one target, referred to as outside body parts, are less exposed to treatment radiation at least to a predetermined extent in the case of subsequent radiation therapy treatment of the at least one target and the outside body parts, compared to the case of a treatment which describes a simultaneous treatment of the at least one target and the outside body parts; and determine, by a processor and based on the critical area data and the target data and the treatment beam constraint data and the treatment beam criteria data, target set data describing a set of irradiation targets and spatial information on at least one irradiation region.

* * * * *